United States Patent [19]

Dolling et al.

[11] 3,972,921

[45] Aug. 3, 1976

[54] SYNTHESIS OF RACEMIC 2-DEUTERO-3-FLUORO-ALANINE AND ITS SALTS

[75] Inventors: Ulf-H. Dolling; Edward J. J. Grabowski, both of Westfield; Erwin F. Schoenewaldt, Watchung; Meyer Sletzinger, No. Plainfield, all of N.J.

[73] Assignee: Merck & Co., Inc., Rahway, N.J.

[22] Filed: Nov. 8, 1974

[21] Appl. No.: 522,185

[52] U.S. Cl. .......................... 260/534 C; 260/534 R
[51] Int. Cl.² ................. C07C 99/00; C07C 101/10
[58] Field of Search ......... 260/534 C, 534 R, 585 C

[56] References Cited
UNITED STATES PATENTS

| | | | |
|---|---|---|---|
| 2,610,212 | 9/1952 | Floyd | 260/534 R |
| 2,839,547 | 6/1958 | Berther | 260/534 C X |

FOREIGN PATENTS OR APPLICATIONS

| | | | |
|---|---|---|---|
| 38-6884 | 5/1963 | Japan | 260/534 R |

OTHER PUBLICATIONS

Greenstein et al., Chemistry of the Amino Acids, vol. 3, John Wiley & Sons, Inc., New York, 1961, pp. 1829 and 1830.

*Primary Examiner*—Richard L. Raymond
*Attorney, Agent, or Firm*—Hesna J. Pfeiffer; Henry H. Bassford, Jr.; Julian S. Levitt

[57] ABSTRACT

The racemates of 2-deutero-3-fluoro-alanine and its salts are prepared by reductive amination of 3-fluoropyruvic acid, its hydrate or salts thereof, via the intermediate 2-imino-3-fluoro propionic acid salt, using alkali metal borodeuterides as reducing agents. The racemates thus obtained are valuable in the production of the corresponding 2-deutero-3-fluoro-D-alanine, and its pharmacologically acceptable salts, and derivatives thereof, which are potent antibacterial agents.

7 Claims, No Drawings

SYNTHESIS OF RACEMIC 2-DEUTERO-3-FLUORO-ALANINE AND ITS SALTS

This invention is concerned generally with the production of racemates of 2-deutero-3-fluoro-alanine and its salts, which are valuable as intermediates for preparing 2-deutero-3-fluoro-D-alanine, its salts and esters, potent antibacterial agents effective in inhibiting the growth of pathogenic bacteria of both gram positive and gram negative type. More particularly, it relates to the process for converting 3-fluoro-pyruvic acid, its hydrate or salt thereof to racemic 2-deutero-3-fluoro-alanine by a reductive amination procedure in which a salt of 3-fluoro-pyruvic acid, or hydrate thereof, is subjected to reductive amination with an alkali metal borodeuteride, thereby forming directly a salt of racemic 2-deutero-3-fluoro-alanine; it also relates to the novel 2-imino-3-fluoro-propionate salts and hydrates thereof, intermediates in this reductive amination procedure.

This reductive amination reaction is conveniently conducted by first equilibrating a salt of fluoropyruvic acid hydrate (e.g. lithium 2,2-dihydroxy-3-fluoro-propionate) in aqueous ammoniacal solution with formation of the corresponding salt of 2-imino-3-fluoropropionic acid hydrate (e.g. lithium or sodium 2-hydroxy-2-amino-3-fluoro-propionate); the equilibrium ratio of the hydrated imine thus formed to hydrated pyruvate starting material (i.e. 2,2-dihydroxy-3-fluoro-propionate) is a function of ammonia concentration and, in concentrated aqueous ammonia (13N), the ratio is approximately 95 to 5. Although not ordinarily preferred, lower aqueous ammonia concentrations may be used; for example with 6.5N aqueous ammonium hydroxide, the equilibrium ratio is approximately 90 to 10. Upon reduction, this mixture would necessarily result in a reduced yield of the equilibrium 2-deutero-3-fluoro-alanine and increased amount of 2-deutero-3-fluoro-lactate by-product. The equilibration at 37°C. is a pseudo-first-order reaction with half-life of 15 minutes; equilibration at 37°C. for 90 minutes provides 6 half-lives, and an effective ratio of hydrated imine to hydrated pyruvate of 95 to 5. Although the hydrated 2-imino-3-fluoropropionate salt is not isolated from the ammonia solution, its presence, in a purity of 95%, is readily demonstrated by NMR (nuclear magnetic resonance) measurement.

The hydrated imine (the 2-hydroxy-2-amino-3-fluoro-propionate) is itself in equilibrium, by loss of water, with a minor proportion of the "2-imine" (the 2-imino-3-fluoro-propionate); and the hydrated pyruvate (the 2,2-dihydroxy-3-fluoro-propionate) is likewise in equilibrium, by loss of water, with a minor proportion of the "2-ketone" or "carbonyl" (i.e. the fluoro-pyruvate or 2-keto-3-fluoro-propionate). In the alkali metal borodeuteride reduction operation, it is the 2-imine and carbonyl (not the hydrated forms) which undergo reduction. As "imine" and carbonyl are reduced, the hydrated imine and hydrated carbonyl are rapidly converted to the imine and carbonyl, respectively. The discovery that the 2-imine can be efficiently reduced to the "2-amine" using an alkali metal borodeuteride, and particularly that this reduction can be conducted in aqueous solution and even in the presence of concentrated aqueous ammonia, was indeed surprising.

Moreover, the desired reduction of the imine group to form 2-deutero-3-fluoro-alanine proceeds much more slowly than does the reduction of carbonyl to form 2-deutero-3-fluoro-lactate. Accordingly, concentrated aqueous ammonia is ordinarily employed in the initial equilibration reaction to achieve the highest ratio of hydrated imine to hydrated pyruvate (i.e. 95:5), and the reduction reaction is conducted as rapidly as possible, relative to the rate of reverse equilibration* of the hydrated imine to hydrated pyruvate. This rapid reduction may be accomplished by using a large (up to fivefold) excess alkali metal borodeuteride reducing agent.

* This reversal of hydrated imine to hydrated pyruvate necessarily occurs when the carbonyl group, due to its more rapid reduction, is preferentially removed from the reaction solution.

It is preferred, however, to employ only a small (i.e. 50%) excess of the costly borodeuteride reducing agent; under such circumstances, the rate of reduction of imine would be reduced, the reverse equilibration could occur to a very considerable degree, and formation of the unwanted by-product 2-deutero-3-fluoro-lactate would be substantially increased. It is a preferred embodiment of this invention, that this unwanted reverse equilibration can be minimized while employing only a 50% excess of borodeuteride reducing agent. This is achieved by adding the borodeuteride reducing agent to the equilibrium solution, and then rapidly evaporating excess ammonia from the solution; at the resulting reduced pH (corresponding to substantial removal of excess ammonia), the borodeuteride reduction is extremely rapid. It is a feature of the invention that the evaporative removal of the ammonia be accomplished sufficiently rapidly so that the thereby greatly accelerated borodeuteride reduction effectively reduces all imine to amine before there can occur any substantial reverse equilibration of hydrated imine to hydrated pyruvate (which would otherwise result from this reduced ammonia concentration). While with flash evaporating equipment, the parameters above indicated can be readily achieved at room temperature or above, it has been found convenient in batch operations to "freeze" the equilibrium at 95 parts hydrated imine to 5 parts hydrated pyruvate in concentrated aqueous ammonia by cooling the mixture to 10°C., at which temperature the equilibration half-life (which is 15 minutes at 37°C.) is increased to approximately 5 hours; the borodeuteride reducing agent is then added to the cold solution. Although, in this concentrated aqueous ammonia solution at 10°C., the rate of borodeuteride reduction of imine is relatively slow, the rate of reduction (using this low temperature and small excess borodeuteride reducing agent) is greatly increased (so that the reduction of imine to amine (i.e. to 2-deutero-3-fluoro-DL-alanine, occurs in a period of only 10 minutes) by evaporative removal of excess ammonia; such evaporation is conducted under reduced pressure while maintaining the temperature at about 10°C. This reaction may be catalyzed, and the yield of 2-deutero-3-fluoro-DL-alanine appreciable increased, by addition of salts such as lithium or sodium salts, as for example lithium chloride or sodium chloride to the reduction reaction mixture.

Thus, the preferred procedure in accordance with the present invention, which effectively combines the above-noted features, involves (a) equilibration of a fluoropyruvate salt, preferably an alkali metal or alkaline earth metal salt, such as calcium fluoropyruvate, sodium fluoropyruvate or lithium fluoropyruvate hydrate*, in concentrated aqueous ammonia, preferably at about 37°C., at which temperature there is obtained in about 90 minutes, a 95:5 ratio of hydrated imine:hydrated pyruvate; (b) addition of alkali metal borodeuteride, such as sodium borodeuteride, lithium borodeuteride, and the like, after cooling to 10°C., if desired, to freeze the equilibrium; (c) evaporative removal of excess ammonia sufficiently rapidly so that accelerated borodeuteride reduction effectively reduces imine to amine before substantial reverse equilibration occurs to form hydrated pyruvate; at the preferred 10°C. temperature, equilibration half-life is increased to 5 hours, whereas complete reduction of imine to amine occurs in only about 10 minutes. The reduction may be conducted, if desired, at room temperature or above without evaporating excess ammonia from the concentrated aqueous ammonia solution, but this procedure results in poorer yields. Salts, such as lithium chloride or sodium chloride, which catalyze the reduction and increase the yield of 2-deutero-3-fluoro-DL-alanine, may be incorporated in the reaction mixture if desired.

* It is particularly advantageous to employ the novel lithium fluoropyruvate hydrate, since the latter, in contrast to other alkali metal fluoro-pyruvates, is relatively insoluble in water and is prepared, in accordance with the presently invented process, in pure form and in high yield.

Following the reductive amination reaction, the reaction mixture is evaporated in vacuo until water distills, thereby substantially removing all ammonia present, since residual ammonium ions transfer in the ion-exchange column purification. The substantially ammonia-free reaction solution is then acidified with an aqueous mineral acid, such as aqueous hydrochloric acid, thereby cleaving the boron complex of 2-deutero-3-fluoro-alanine formed during the reductive amination reaction. The acidified reaction mixture, which is conveniently freed of any colored impurities which may be present by treatment with activated charcoal, is then passed through a column containing an acid pre-washed, strongly-acidic, cation-exchange resin, such as Dowex 50W-X4 or Dowex 50W-X8* thereby separating the desired 2-deutero-3-fluoro-alanine from the byproduct fluorolactic acid and metallic cations. The ion exchange column containing the adsorbed 2-deutero-3-fluoro-alanine is washed with de-ionized water until the eluate is no longer acidic, and the column is then eluted with dilute aqeuous ammonium hydroxide solution whereupon ammonium ion replaces the 2-deutero-3-fluoro-alanine on the resin column. The eluate is then evaporated in vacuo, thereby removing any ammonia present in the eluate; the colored solution is decolorized with activated charcoal; the decolorized solution is evaporated in vacuo; and the residual material is crystallized from aqueous alkanol, preferably aqueous isopropanol, to give the 2-deutero-3-fluoro-alanine in substantially pure form.

*Dowex 50W-X4 is a strongly-acidic cation-exchange resin consisting of a sulfonated styrene-divinylbenzene copolymer containing 4% divinylbenzene, having a mesh size of 20-50 mesh, based on the U.S. standard screen; Dowex 50W-X8 is similar to Dowex 50W-X4 except that it contains 8% divinylbenzene in the sulfonated styrene-divinylbenzene copolymer.

The following examples illustrate methods of carrying out the present invention, but it is to be understood that these examples are given for purposes of illustration and not of limitation.

EXAMPLE 1

To about 150 ml. of concentrated aqueous ammonium hydroxide is added, with good agitation and at room temperature, 18.35 grams of lithium fluoropyruvate hydrate, which can be prepared as described hereinabove. The resulting suspension is heated to about 35°–37°C. (whereupon substantially all of the solid material dissolves), and the solution is maintained at that temperature for a period of about 1.5 hours. The resulting solution which may be dark in color is cooled to about 10°C., and to this cold solution is added 1.785 grams of sodium borodeuteride. The resulting solution is placed under vacuum with stirring and vigorous subsurface nitrogen flow to remove dissolved ammonia. Temperature of the solution is maintained at 10°–13°C. for a period of about 1 hour, then gradually raised to about 25°C. over a 1 hour period, and held at 28°–33°C. for a period of about 1.5 hours. The reaction solution is evaporated in vacuo at 35°C. until water distills and solution is essentially free of ammonia, and the resulting solution is then acidified with about 80 ml. of 2.5 N aqueous hydrochloric acid solution. The acidified reaction solution is stirred with about 2.5 grams of activated charcoal (Darco KB) for about 15 minutes and filtered.

The filtered solution is slowly passed through a column containing 850 ml. of acid pre-washed, strongly acidic, cation-exchange resin (Dowex 50W-X4). The column is washed with de-ionized water until the eluate is no longer acidic (about 4 liters water required), and the column is then eluted with 0.5 N aqueous ammonium hydroxide solution. The ninhydrinpositive fractions are combined, and evaporated in vacuo at a temperature not exceeding 30°C., to give about 400 ml. of an ammonia-free solution. This solution is stirred at room temperature with 2.5 grams of activated charcoal (Darco KB); the charcoal is removed by filtration, the filtered solution is again stirred with an additional 1.5 grams of activated charcoal, and the slurry is again filtered. The filtered solution is evaporated to dryness in vacuo at a temperature not exceeding 30°C. to give about 7.3 grams of crude material.

This material is dissolved in 33 ml. of water at a temperature of about 60°C.; about 27 ml. of isopropanol (preheated to 60°C.) is added; the aqueous isopropanol solution is seeded with crystals of 2-deutero-3-fluoro-DL-alanine; and the resulting mixture is cooled slowly first to room temperature and then to about 0°C. The crystalline slurry is allowed to stand at 0°C. for about 1–2 hours, the slurry is filtered, and the crystalline material on the filter is washed with two 5-ml. portions of 90% aqueous isopropanol, then with 5 ml.-portions of isopropanol, and finally with hexane. The washed material is dried in vacuo at a temperature of 50°–60°C. to give about 5.6 grams of 2-deutero-3-fluoro-DL-alanine.

EXAMPLE 2

A mixture of 1.79 grams (13 millimoles) of lithium fluoropyruvate hydrate and 19.5 ml. of 6.5N aqueous ammonia is maintained at 37°C., with stirring for 2 hours, cooled to 25°C., and to the cooled solution is added 600 mg. (13.8 millimoles) of lithium chloride and 231 mg. (5.5 millimoles) of sodium borodeuteride. The resulting solution is heated at 37°C. for 2 hours.

The reaction mixture is evaporated in vacuo thereby removing excess ammonia, acidified with 10 ml. of 2.5N hydrochloric acid, and the solution is decolorized by treatment with 0.2 g. activated charcoal (Darco KB). The decolorized solution is applied to a column of 100 ml. of strongly-acidic, cation-exchange resin (Dowes 50W-X8) on the hydrogen cycle, the column is washed with 500 ml. of distilled water, and the product eluted with 0.5N aqueous ammonium hydroxide. Ninhydrin-positive fractions are combined and evaporated to dryness in vacuo. This residual material is dissolved in about 3.6 ml. of water at 60°C., and crystallized by addition of 2.3 ml. of isopropanol. The resulting crystalline slurry is allowed to stand at a temperature of 0°–5°C. for one hour, filtered, and the white crystalline product dried in vacuo to give about 0.5 grams of substantially pure 2-deutero-3-fluoro-DL-alanine.

The lithium fluoro-pyruvate hydrate used as starting material in Examples 1 and 2 may be prepared as follows: A mixture of 400 ml. of ethyl ether and 240 ml. of 5N aqueous hydrochloric acid is cooled to a temperature of about −15° to −20°C. To this mixture is added, with good stirring and under a nitrogen atmosphere, about 138 grams of lump-free ethyl ethoxyalyl-fluoroacetate sodium salt at a steady rate such that the temperature remains beween about −15°C. and −20°C. When addition is complete, the mixture is warmed to room temperature, diluted with 240 ml. of water, and the aqueous-ethereal mixture is heated at atmospheric pressure and the ether distilled until temperature of aqueous solution reaches about 102°–105°C. The resulting aqueous solution is then heated under reflux for a period of about 4 hours. The reaction solution is cooled to room temperature, stirred with about 6 grams of activated charcoal (Darco G-60), filtered through acid-prewashed diatomaceous silica (Supercel), and the insoluble material on the filter washed with a minimum of water. The filtered solution is cooled to about 0°–5°C.; neutralized with pH control, by addition of solid lithium hydroxide hydrate (about 47 grams of $LiOH.H_2O$ required) to a final pH of 6.0 to 6.5; and the resulting neutralized slurry is allowed to stand at about 0°C. for a period of approximately 15 hours. The precipitated material is recovered by filtration, washed with a minimum of cold water, then with two 200 ml.-portions of methanol, and then with two 200 ml.-portions of acetone. The resulting material is air-dried to give about 56 grams of lithium fluoropyruvate hydrate.

Various changes and modifications may be made in carrying out the present invention without departing from the spirit and scope thereof. Insofar as these changes and modifications are within the purview of the annexed claims, they are to be considered as part of this invention.

What is claimed is:

1. The process which comprises reacting an alkali metal or alkaline earth metal salt of 3-fluoro-pyruvic acid or hydrate thereof, with aqueous ammonium hydroxide until substantially converted to a salt of 2-imino-3-fluoro-propionic acid hydrate, and reacting the latter with an alkali metal borodeuteride to produce a salt of 2-deutero-3-fluoro-DL-alanine.

2. The process, as defined in claim 1, which comprises reacting a salt of 3-fluoro-pyruvic acid hydrate with concentrated aqueous ammonium hydroxide for a time sufficient to convert substantially all of the 3-fluoro-pyruvic acid compound to a salt of hydrated 2-imino-3-fluoro-propionic acid, cooling the resulting solution to a temperature of about 10°C. thereby substantially stabilizing the 2-3-fluoropropionic acid component of said solution against the reverse reaction to form 3-fluoro-pyruvic acid compound, adding alkali metal borodeuteride to this cold aqueous ammoniacal solution and subjecting the resulting solution to distillation under reduced pressure while maintaining the temperature at about 10°C. until substantially all of the excess ammonia is evaporated from said solution, and maintaining the resulting solution at 10°C. for a period of about 10 minutes at the end of which time the reduction of the 2-imino substituent is substantially complete to form a salt of 2-deutero-3-fluoro-DL-alanine.

3. The process, as defined in claim 1, which comprises reacting lithium 3-fluoro-pyruvate hydrate with concentrated aqueous ammonium hydroxide at a temperature at about 37°C. for a period of about 90 minutes thereby forming an equilibrium solution containing about 95 parts of hydrated 2-imino-3-fluoro-propionate salt and about 5 parts of hydrated 3-fluoro-pyruvate salt; cooling the resulting aqueous ammoniacal solution to a temperature of about 10°C. thereby substantially stabilizing the 2-imino-3-fluoro-propionate component against the reverse reaction to form 3-fluoropyruvate; adding to this cold aqueous ammoniacal solution approximately 1.5 equivalents of sodium borodeuteride; subjecting the resulting solution to distillation under reduced pressure at 10°C. until substantially all of the excess ammonia is evaporated; and maintaining the resulting solution at 10°C. for a period of about 10 minutes, at the end of which time the reduction of the 2-imino substituent is substantially complete, to produce a salt of 2-deutero-3-fluoro-DL-alanine.

4. The process which comprises reacting a 2-imino-3-fluoro-propionic acid compound with alkali metal borodeuteride to produce a 2-deutero-3-fluoro-DL-alanine compound.

5. The process, as defined in claim 4, which comprises reacting a salt of hydrated 2-imino-3-fluoro-propionic acid with sodium borodeuteride thereby forming a salt of 2-deutero-3-fluoro-DL-alanine.

6. The process, as defined in claim 4, which comprises bringing together in aqueous ammonia solution a salt of 2-hydroxy-2-amino-3-fluoro-propionic acid and an alkali metal borodeuteride, and evaporating excess ammonia from said solution, thereby forming a salt of 2-deutero-3-fluoro-DL-alanine.

7. The process, as defined in claim 4, which comprises bringing together in an aqueous solution substantially free of excess ammonia, a lithium salt of hydrated 2-imino-3-fluoro-propionic acid and sodium borodeuteride thereby reducing the 2-imino substituent to form a lithium salt of 2-deutero-3-fluoro-DL-alanine.

* * * * *

UNITED STATES PATENT OFFICE
CERTIFICATE OF CORRECTION

PATENT NO. : 3,972,921
DATED : August 3, 1976
INVENTOR(S) : ULF-H. DOLLING et al.

It is certified that error appears in the above-identified patent and that said Letters Patent are hereby corrected as shown below.

In Col. 6, Claim 2, line 5, delete "2,3-fluoropropionic acid" and insert in place thereof -- 2-imino-3-fluoro-propionic acid --.

Signed and Sealed this

Nineteenth Day of October 1976

[SEAL]

*Attest:*

RUTH C. MASON
*Attesting Officer*

C. MARSHALL DANN
*Commissioner of Patents and Trademarks*